United States Patent
Bao et al.

(10) Patent No.: US 12,017,809 B1
(45) Date of Patent: Jun. 25, 2024

(54) DEVICE FOR DETECTING CARBON EMISSION OF PASSIVE HOUSE

(71) Applicant: Hangzhou City University, Zhejiang (CN)

(72) Inventors: Haijun Bao, Zhejiang (CN); Ning Wang, Zhejiang (CN)

(73) Assignee: Hangzhou City University, Zhejiang (CN)

( * ) Notice: Subject to any disclaimer, the term of this patent is extended or adjusted under 35 U.S.C. 154(b) by 0 days.

(21) Appl. No.: 18/004,677

(22) PCT Filed: Oct. 25, 2022

(86) PCT No.: PCT/CN2022/127277
§ 371 (c)(1),
(2) Date: Jan. 9, 2023

(87) PCT Pub. No.: WO2024/065915
PCT Pub. Date: Apr. 4, 2024

(30) Foreign Application Priority Data

Sep. 28, 2022  (CN) .......................... 202211206505.4

(51) Int. Cl.
*B64U 10/14* (2023.01)
*B64U 20/80* (2023.01)
(Continued)

(52) U.S. Cl.
CPC ............. *B64U 10/14* (2023.01); *B64U 20/80* (2023.01); *B64U 60/40* (2023.01); *B64U 60/50* (2023.01); *B64U 2101/00* (2023.01)

(58) Field of Classification Search
CPC ........ B64U 10/14; B64U 20/80; B64U 60/40; B64U 60/50; B64U 2101/00; G01N 33/00; G01N 33/1846
See application file for complete search history.

(56) References Cited

U.S. PATENT DOCUMENTS 5,473,162 A * 12/1995 Busch ..................... G01N 21/72
250/339.08
7,587,926 B2 * 9/2009 Ackerman ............. B65D 83/30
73/1.02
(Continued)

FOREIGN PATENT DOCUMENTS

CN 110758738 A 2/2020
CN 113428068 A 9/2021
(Continued)

*Primary Examiner* — Medhat Badawi
(74) *Attorney, Agent, or Firm* — Avi Avraham Jencmen (57) ABSTRACT

The present disclosure provides a device for detecting carbon emission of a passive house. The device for detecting carbon emission of a passive house is arranged on a metal rain cap at a top of a chimney. The device for detecting carbon emission of a passive house includes an unmanned aerial vehicle, a guide assembly, and two landing gear assemblies. The two landing gear assemblies are arranged at a bottom of the unmanned aerial vehicle, the guide assembly is arranged at a bottom of the two landing gear assemblies, and the guide assembly includes two split assemblies. The two split assemblies correspond one-to-one to the two landing gear assemblies, and the split assemblies are in linked connection to the landing gear assemblies. In the device for detecting carbon emission of a passive house, the unmanned aerial vehicle, the guide assembly and the two landing gear assemblies are arranged to cooperate with each other. The present disclosure can have a function of delivering and fixing a device for detecting carbon emission to a chimney by means of an unmanned aerial vehicle, and can further effectively avoid the shielding of the metal rain cap on the chimney and make the detector smoothly correspond to an air outlet of the chimney. The present disclosure is greatly convenient for personnel to use.

9 Claims, 8 Drawing Sheets

(51) Int. Cl.
 B64U 60/40  (2023.01)
 B64U 60/50  (2023.01)
 B64U 101/00 (2023.01)

(56) References Cited

U.S. PATENT DOCUMENTS

| | | | | |
|---|---|---|---|---|
| 9,334,051 | B2* | 5/2016 | Masticola | B64C 39/024 |
| 9,972,212 | B1* | 5/2018 | Sperindeo | G06F 18/22 |
| 10,418,830 | B1* | 9/2019 | Parodi | G05D 1/0202 |
| 10,520,953 | B2* | 12/2019 | Cantrell | G06Q 10/06 |
| 10,642,272 | B1* | 5/2020 | Parodi | B64U 10/13 |
| 10,735,653 | B1* | 8/2020 | Huang | G06V 10/243 |
| 11,603,219 | B2* | 3/2023 | Ratajczak | B64D 1/22 |
| 11,618,565 | B2* | 4/2023 | Blake | B60L 53/53 |
| | | | | 701/3 |
| 11,671,888 | B2* | 6/2023 | Kaneda | B64C 39/02 |
| | | | | 370/331 |
| 11,673,690 | B2* | 6/2023 | Dayan | B64U 10/60 |
| | | | | 244/114 R |
| 11,776,136 | B1* | 10/2023 | Pachikov | B64U 70/92 |
| | | | | 244/17.23 |
| 11,840,329 | B1* | 12/2023 | Hinman | B64D 27/24 |
| 11,869,363 | B1* | 1/2024 | Kunkel | B64U 50/19 |
| 11,892,563 | B1* | 2/2024 | Mistry | G01S 13/003 |
| 11,939,080 | B2* | 3/2024 | Cowden | B64U 80/30 |
| 2004/0119631 | A1* | 6/2004 | Sanders | G01S 7/38 |
| | | | | 342/14 |
| 2012/0261516 | A1* | 10/2012 | Gilliland | G01S 7/4868 |
| | | | | 356/4.01 |
| 2013/0056230 | A1* | 3/2013 | Lemke | A62C 3/0242 |
| | | | | 169/44 |
| 2013/0292512 | A1* | 11/2013 | Erben | B64C 39/024 |
| | | | | 244/1 R |
| 2015/0246727 | A1* | 9/2015 | Masticola | B64C 39/024 |
| | | | | 701/2 |
| 2016/0035224 | A1* | 2/2016 | Yang | G08G 5/0069 |
| | | | | 701/23 |
| 2016/0200207 | A1* | 7/2016 | Lee | B64C 39/024 |
| | | | | 244/17.23 |
| 2017/0021923 | A1* | 1/2017 | Fisher | B64F 1/12 |
| 2017/0144776 | A1* | 5/2017 | Fisher | B64F 1/24 |
| 2017/0210486 | A1* | 7/2017 | O'Brien | H04N 23/55 |
| 2017/0217323 | A1* | 8/2017 | Antonini | B60L 53/30 |
| 2017/0253330 | A1* | 9/2017 | Saigh | G08G 5/0069 |
| 2017/0283090 | A1* | 10/2017 | Miller | B64U 50/39 |
| 2018/0118340 | A1* | 5/2018 | Russo | A01K 59/00 |
| 2018/0349745 | A1* | 12/2018 | Fryshman | A01M 1/026 |
| 2019/0019066 | A1* | 1/2019 | Fryshman | A01M 7/00 |
| 2019/0106224 | A1* | 4/2019 | Nishikawa | B64U 50/37 |
| 2019/0128862 | A1* | 5/2019 | Willett | B64C 39/024 |
| 2019/0180151 | A1* | 6/2019 | Fryshman | A01M 1/2094 |
| 2020/0064135 | A1* | 2/2020 | Lai | G08G 5/0069 |
| 2020/0073385 | A1* | 3/2020 | Jobanputra | G06N 3/08 |
| 2020/0262583 | A1* | 8/2020 | Ducharme | B64C 25/32 |
| 2020/0263285 | A1* | 8/2020 | Stowell | C23C 4/067 |
| 2020/0302243 | A1* | 9/2020 | Fryshman | B64C 39/024 |
| 2020/0355599 | A1* | 11/2020 | Rodier | G01N 15/1434 |
| 2021/0300547 | A1* | 9/2021 | Stanhope | B64F 1/12 |
| 2021/0300552 | A1* | 9/2021 | Isberg | B64U 70/93 |
| 2021/0385388 | A1* | 12/2021 | Utter | G01S 5/163 |
| 2022/0019970 | A1* | 1/2022 | Williams | B64U 60/50 |
| 2022/0091026 | A1* | 3/2022 | Scott | G01N 33/0036 |
| 2022/0153413 | A1* | 5/2022 | Riccardo | G01S 17/66 |
| 2022/0161251 | A1* | 5/2022 | Spaventa | G01N 33/487 |
| 2022/0187827 | A1* | 6/2022 | Graham | B64U 10/13 |
| 2022/0237909 | A1* | 7/2022 | Nurkic Kacapor | G06V 10/82 |
| 2022/0355952 | A1* | 11/2022 | Thompson | B64C 27/32 |
| 2022/0411056 | A1* | 12/2022 | Pratt, Jr. | G05D 1/0094 |
| 2022/0413518 | A1* | 12/2022 | Lee | B64C 39/02 |
| 2023/0040722 | A1* | 2/2023 | Stowell | C22C 19/05 |
| 2023/0145800 | A1* | 5/2023 | Stowell | C23C 16/513 |
| | | | | 428/408 |
| 2023/0167653 | A1* | 6/2023 | Waters | G08G 5/0013 |
| | | | | 244/114 R |
| 2023/0202663 | A1* | 6/2023 | Palombini | B60L 53/62 |
| | | | | 701/3 |
| 2023/0202670 | A1* | 6/2023 | Bosma | B64D 1/06 |
| | | | | 244/195 |
| 2023/0205231 | A1* | 6/2023 | Romar | G05D 1/101 |
| | | | | 701/2 |
| 2023/0223142 | A1* | 7/2023 | Joao | H04N 7/141 |
| | | | | 705/2 |
| 2024/0003244 | A1* | 1/2024 | Debs | E21B 47/10 |
| 2024/0004361 | A1* | 1/2024 | Morris | G05B 15/02 |
| 2024/0012760 | A1* | 1/2024 | Farhadiroushan | G06F 12/0246 |
| 2024/0071196 | A1* | 2/2024 | Joao | B64U 10/00 |
| 2024/0090395 | A1* | 3/2024 | Jadhav Siddharth Sunil | B64U 10/13 |

FOREIGN PATENT DOCUMENTS

| | | |
|---|---|---|
| CN | 113844655 A | 12/2021 |
| CN | 216479890 U | 5/2022 |
| CN | 114674979 A | 6/2022 |
| CN | 114926025 A | 8/2022 |

* cited by examiner

DEVICE FOR DETECTING CARBON EMISSION OF PASSIVE HOUSE

TECHNICAL FIELD

The present disclosure relates to the technical field of carbon emission detection apparatuses, in particular a device for detecting carbon emission of a passive house.

BACKGROUND ART

A passive house may also be referred to as a passive energy saving house, and is an energy efficient building built based on a passive design. The passive house can adjust a room to a suitable temperature with very little energy consumption, which is very environmentally friendly. When the passive house is used, carbon will be emitted from an air outlet, so when the passive house is put into production, it is necessary to detect carbon emission of the passive house. However, when detecting the carbon emission of the passive house, it is inconvenient and dangerous to manually climb to the air outlet and then use an instrument to detect the carbon emission, and there is no corresponding improvement on this defect.

SUMMARY

(I) Solved Technical Problem

As for the defect in the prior art, the present invention provides a device for detecting carbon emission of a passive house.

(II) Technical Solution

In order to achieve the above objective, the present disclosure is achieved by means of the following technical solution: a device for detecting carbon emission of a passive house is arranged on a metal rain cap at a top of a chimney. The device for detecting carbon emission of a passive house includes an unmanned aerial vehicle, a guide assembly, and two landing gear assemblies. The two landing gear assemblies are arranged at a bottom of the unmanned aerial vehicle, the guide assembly is arranged at a bottom of the two landing gear assemblies, and the guide assembly includes two split assemblies. The two split assemblies correspond one-to-one to the two landing gear assemblies, and the split assemblies are in linked connection to the landing gear assemblies. The split assemblies includes a plurality of metal guide rings small to large, and a connection strap. The connection strap is arranged between two adjacent metal guide rings, and the plurality of metal guide rings are movably sleeved with each other. The device further includes a fixed gripping assembly, and the fixed gripping assembly is movably arranged at the bottom of the unmanned aerial vehicle.

Preferably, each landing gear assembly includes a ring seat, a snap joint, a gear seat and a transverse telescopic rod. The transverse telescopic rods are arranged at the bottom of the unmanned aerial vehicle transversely, and the gear seats are arranged at moving ends of the transverse telescopic rods. The snap joints are arranged at bottoms of the gear seats, and the ring seats are detachably snapped onto the snap joints. The ring seats are connected to the split assemblies.

Preferably, each landing gear assembly further includes an electromagnet, and the electromagnets are arranged on the gear seats. The two electromagnets located on different gear seats are attracted to each other.

Preferably, the fixed gripping assembly includes a metal cap head and a main lead. One end of the main lead is arranged at the bottom of the unmanned aerial vehicle, and the other end is detachably snapped to the metal cap head. The metal cap head is in linked connection to the split assemblies.

Preferably, the fixed gripping assembly further includes four air detectors and inwardly curved multi-segment folding stands. The four multi-segment folding stands are hinged at equal angles on the metal cap head with the metal cap head as a center. The air detectors are arranged on one ends of the multi-segment folding stands away from the metal cap head.

Preferably, the fixed gripping assembly further includes four guide plates. The guide plates are arranged outside the air detectors. The guide plates have a width greater than a gap distance between two adjacent metal guide rings.

Preferably, the device for detecting carbon emission of a passive house further includes two snap belts and a snap base, and the snap base is arranged on the metal guide ring with a smallest caliber. One ends of the snap belts are detachably snapped on the snap base, and the other ends are connected to the metal cap head.

Preferably, the split assemblies further include a plurality of secondary leads. The plurality of secondary leads correspond one-to-one to the plurality of metal guide rings. One ends of the secondary leads are electrically connected to the metal guide rings, and the other ends are connected to the metal cap head by means of the main lead in series.

Preferably, the device for detecting carbon emission of a passive house further includes a plurality of abutting plates and telescopic rods, and the plurality of telescopic rods correspond one-to-one to the plurality of air detectors. The telescopic rods are arranged on the unmanned aerial vehicle vertically, moving ends of the telescopic rods penetrate the unmanned aerial vehicle and extend to the bottom of the unmanned aerial vehicle. The abutting plates are arranged on the moving ends of the telescopic rods. The abutting plates correspond to the air detectors.

(III) Beneficial Effect

The present disclosure provides a device for detecting carbon emission of a passive house. The present disclosure has the following beneficial effects:

1. In the device for detecting carbon emission of a passive house, an unmanned aerial vehicle, a guide assembly and two landing gear assemblies are arranged to cooperate with each other. The present disclosure may have a function of delivering and fixing a device for detecting carbon emission to a chimney by means of an unmanned aerial vehicle, and may further effectively avoid the shielding of the metal rain cap on the chimney and make the detector smoothly correspond to an air outlet of the chimney. The present disclosure is greatly convenient for personnel to use.

In the figures: 1 chimney, 2 metal rain cap, 3 guide assembly, 4 telescopic rod, 5 unmanned aerial vehicle, 6 landing gear assembly, 7 split assembly, 8 electromagnet, 9 ring seat, 10 transverse telescopic rod, 11 metal guide ring, 12 gear seat, 13 snap joint, 14 abutting plate, 15 air detector, 16 fixed gripping assembly, 17 connection strap, 18 metal cap head, 19 main lead, 20 secondary lead, 21 multi-segment folding stand, 22 guide plate, 23 snap belt, and 24 snap base.

DETAILED DESCRIPTION OF THE EMBODIMENTS

Figure 1:
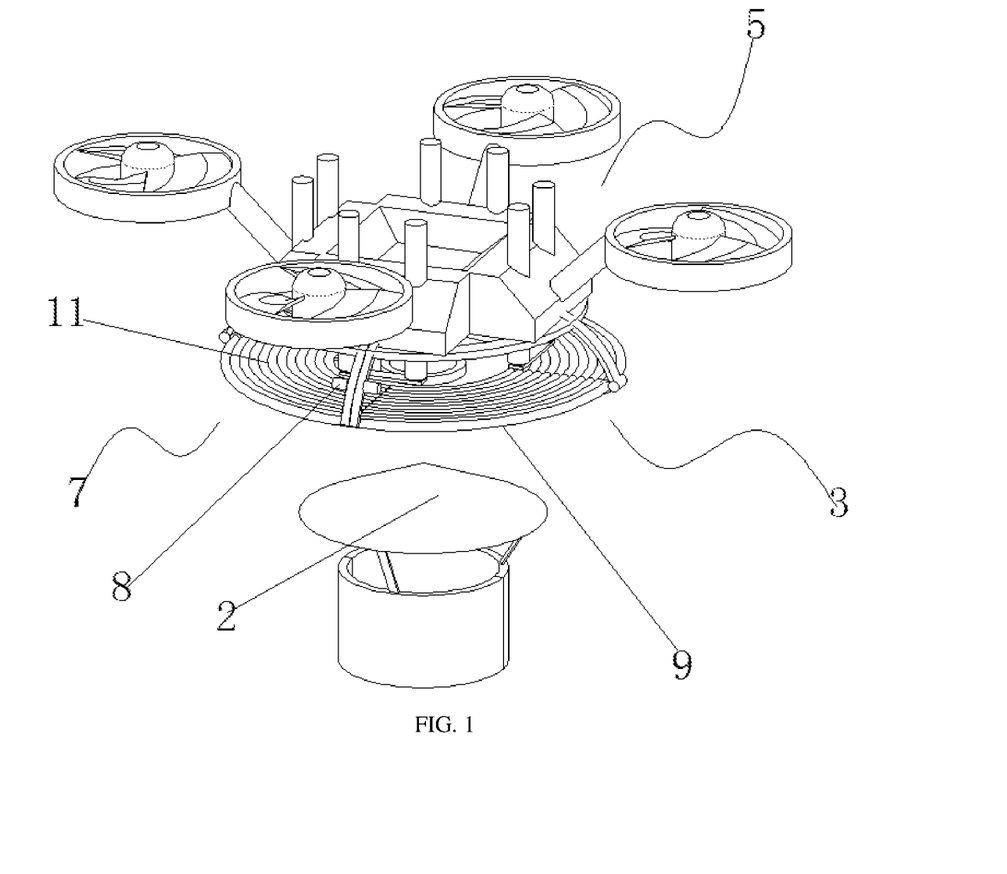
FIG. 1 is a first perspective view according to the present disclosure.
Figure 2:
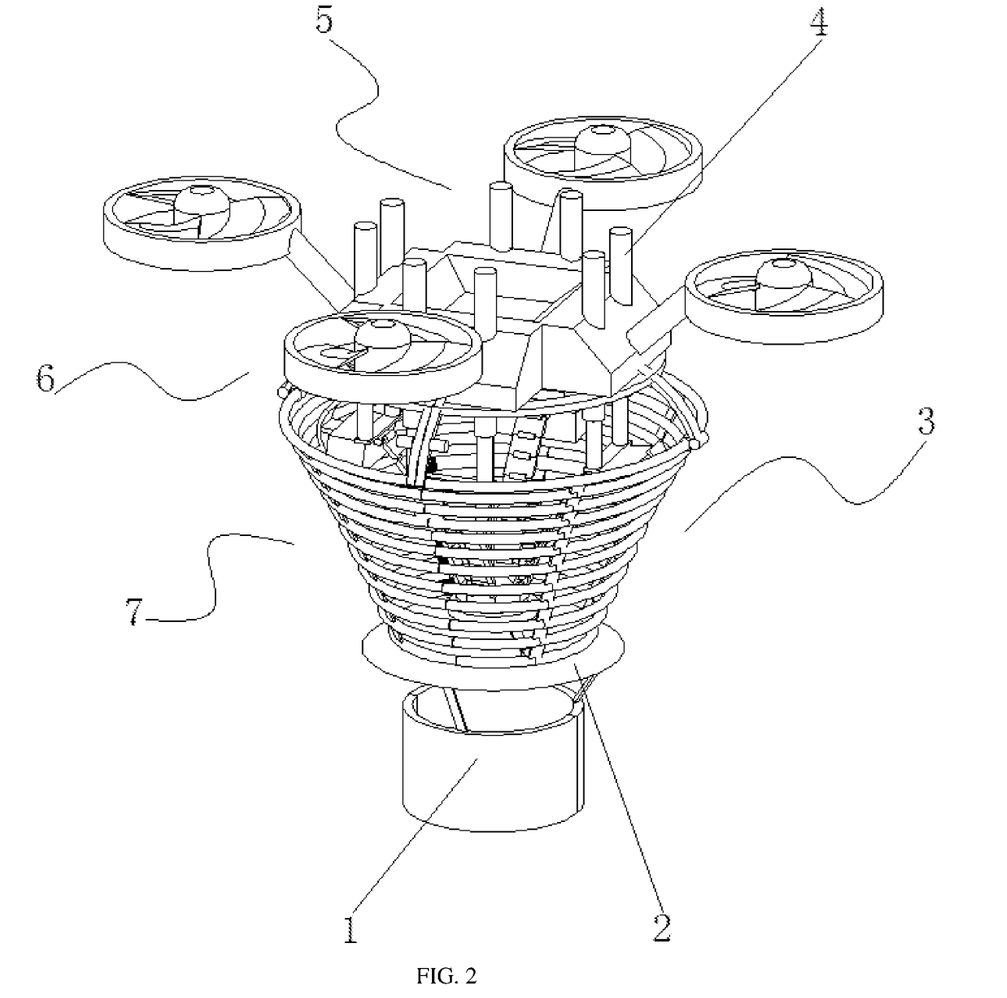
FIG. 2 is a second perspective view according to the present disclosure.
Figure 3:
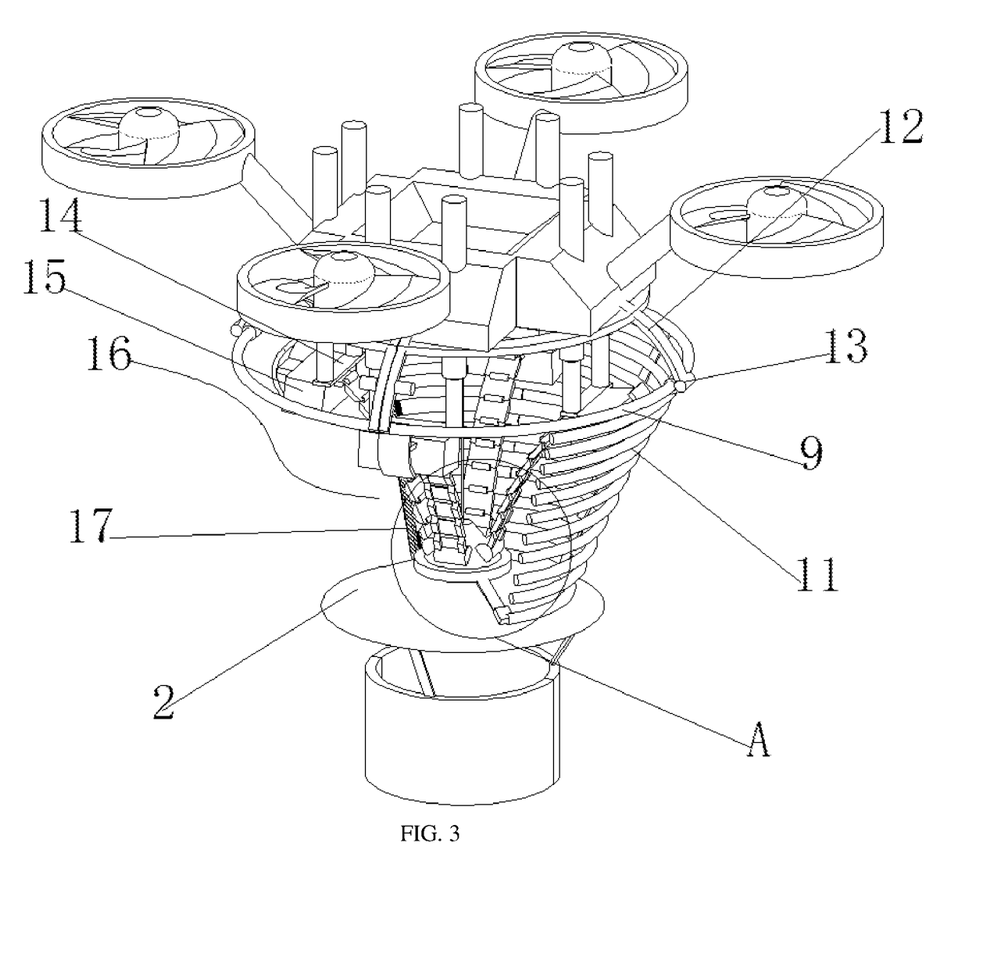
FIG. 3 is a third perspective view according to the present disclosure.
Figure 4:
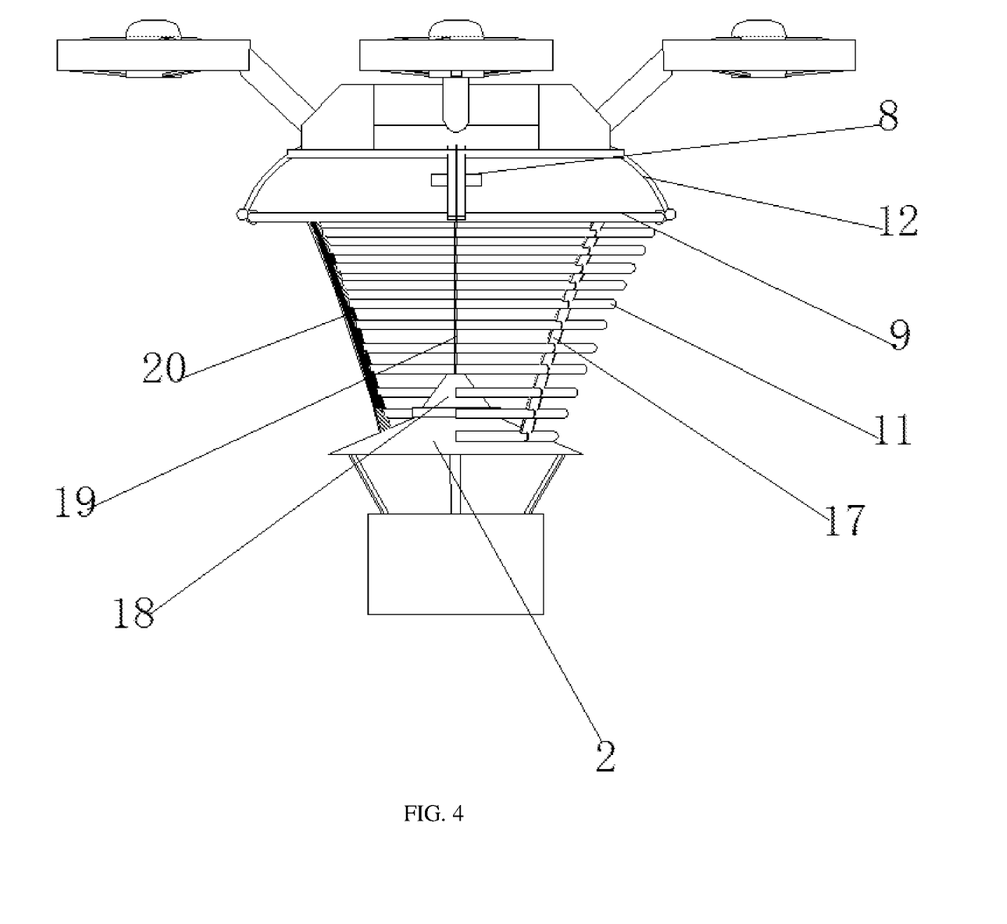
FIG. 4 is a front sectional view according to the present disclosure.
Figure 5:
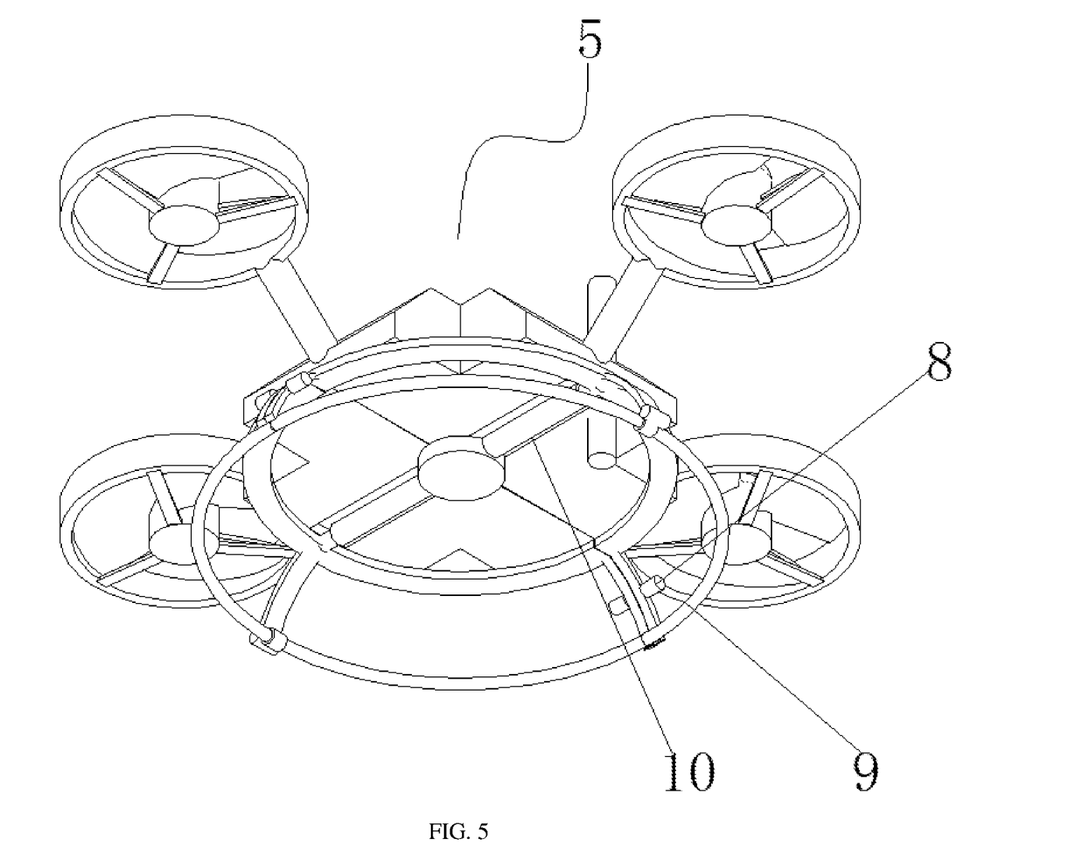
FIG. 5 is a first perspective view of a partial component according to the present disclosure.
Figure 6:
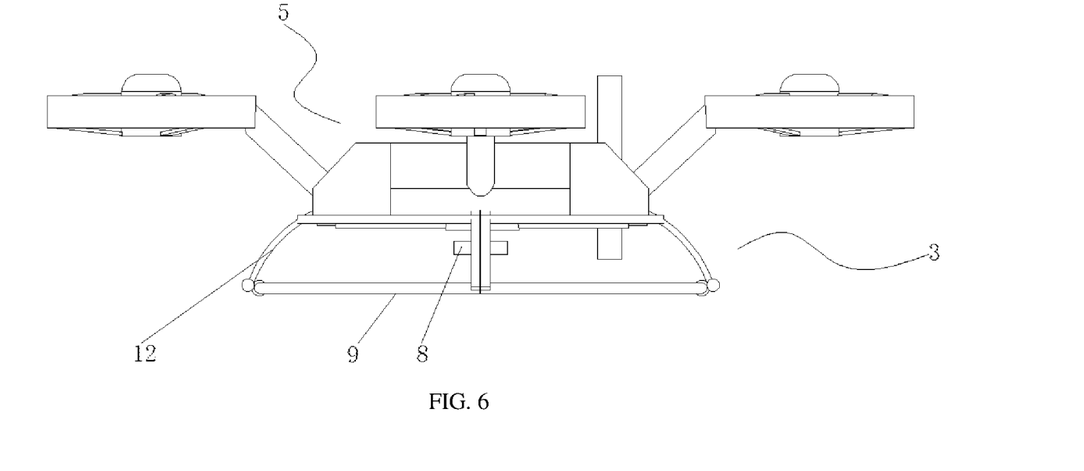
FIG. 6 is a first front view of a partial component according to the present disclosure.
Figure 7:
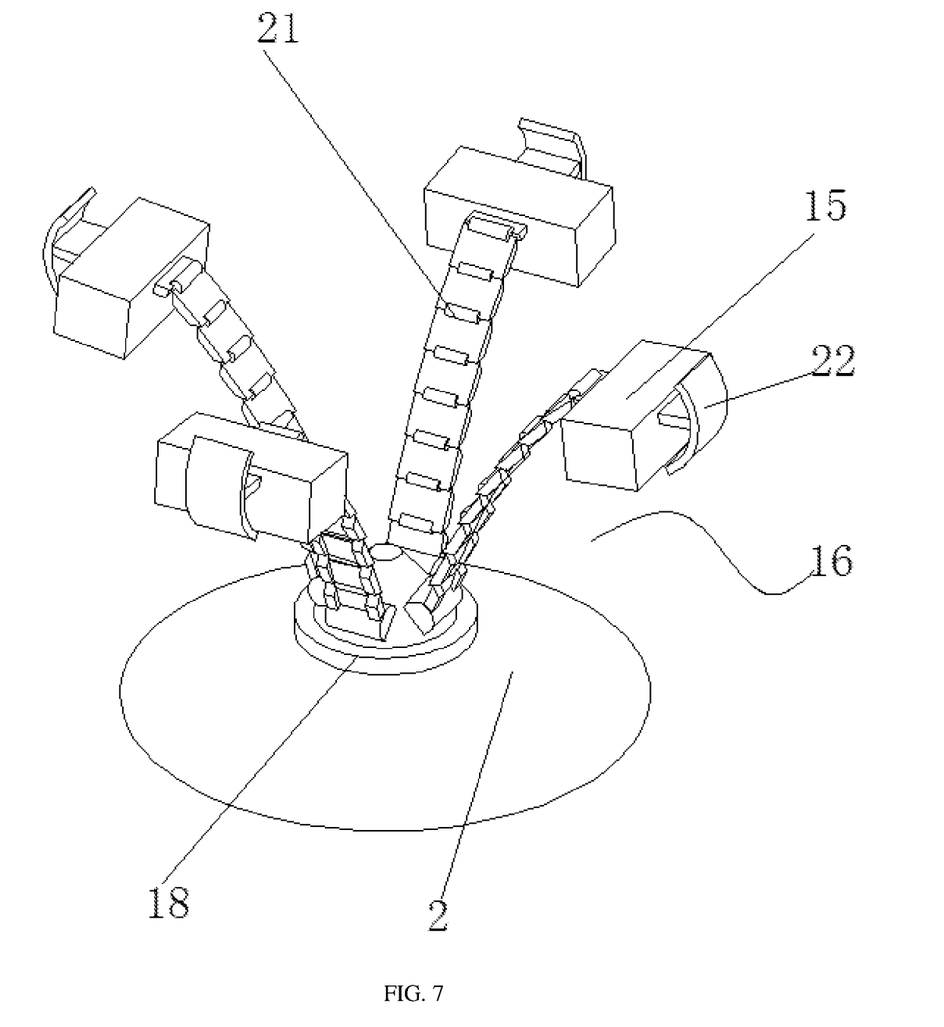
FIG. 7 is a second perspective view of a partial component according to the present disclosure.
Figure 8:
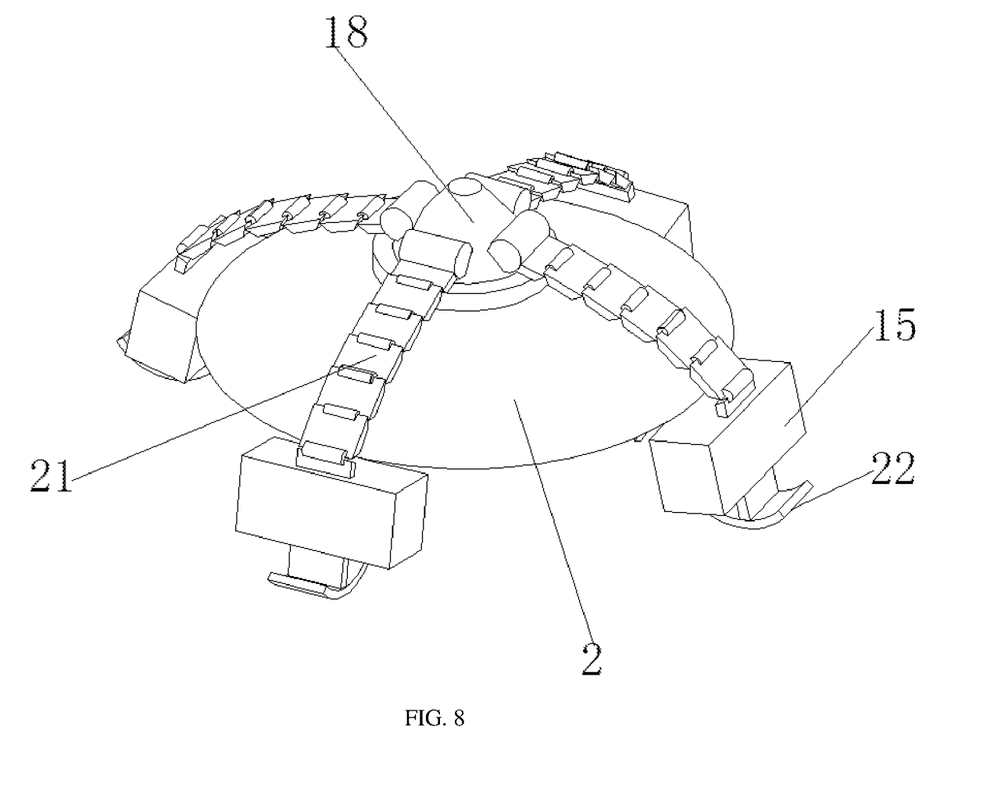
FIG. 8 is a third perspective view of a partial component according to the present disclosure.
Figure 9:
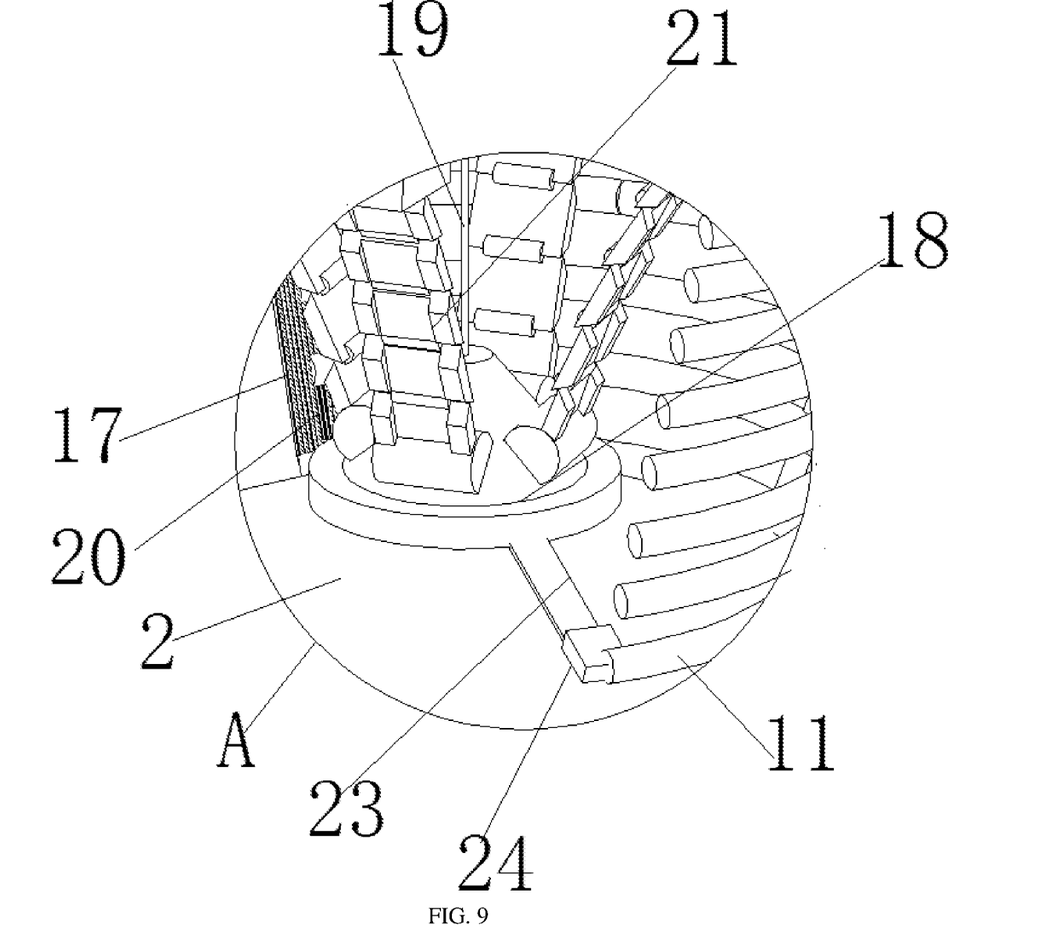
FIG. 9 is an enlarged diagram of A in FIG. 2 according to the present disclosure.

An example of the present disclosure provides a device for detecting carbon emission of a passive house. As shown in FIGS. 1-9, the device for detecting carbon emission of a passive house is arranged on a metal rain cap 2 at a top of a chimney 1. The device for detecting carbon emission of a passive house includes an unmanned aerial vehicle 5, a guide assembly 3, and two landing gear assemblies 6. The two landing gear assemblies 6 are arranged on a bottom of the unmanned aerial vehicle 5, the guide assembly 3 is arranged on a bottom of the two landing gear assemblies 6, and the guide assembly 3 includes two split assemblies 7. The two split assemblies 7 correspond one-to-one to the two landing gear assemblies 6, and the split assemblies 7 are in linked connection to the landing gear assemblies 6. The split assemblies 7 includes a plurality of metal guide rings 11 small to large, and a connection strap 17. The connection strap 17 is arranged between two adjacent metal guide rings 11, and the plurality of metal guide rings 11 are movably sleeved with each other. The device further includes a fixed gripping assembly 16, and the fixed gripping assembly 16 is movably arranged at the bottom of the unmanned aerial vehicle 5.

By arranging the plurality of metal guide rings 11 small to large and a connection strap 17 cooperating with each other, a diameter of the metal rain cap 2 may be physically measured by making different sizes of metal guide rings 11 make contact with an outer surface of the metal rain cap 2. In this way, the fixed gripping assembly 16 may be conveniently adjusted, so as to effectively guarantee that the air detectors 15 correspond to an air outlet of (1) for ease of use by personnel.

Each landing gear assembly 6 includes a ring seat 9, a snap joint 13, a gear seat 12 and a transverse telescopic rod 10. The transverse telescopic rods 10 are arranged at the bottom of the unmanned aerial vehicle 5 transversely, and the gear seats 12 are arranged at moving ends of the transverse telescopic rods 10. The snap joints 13 are arranged at bottoms of the gear seats 12, and the ring seats 9 are detachably snapped onto the snap joints 13. The ring seats 9 are connected to the split assemblies 7.

Each landing gear assembly 6 further includes an electromagnet 8, and the electromagnets 8 are arranged on the gear seats 12. The two electromagnets 8 located on different gear seats 12 are attracted to each other.

The fixed gripping assembly 16 includes a metal cap head 18 and a main lead 19. One end of the main lead 19 is arranged at the bottom of the unmanned aerial vehicle 5, and the other end is detachably snapped to the metal cap head 18. The metal cap head 18 is in linked connection to the split assemblies 7.

The fixed gripping assembly 16 further includes four air detectors 15 and inwardly curved multi-segment folding stands 21. The four multi-segment folding stands 21 are hinged at equal angles on the metal cap head 18 with the metal cap head 18 as a center. The air detectors 15 are arranged on one ends of the multi-segment folding stands 21 away from the metal cap head 18.

The fixed gripping assembly 16 further includes four guide plates 22. The guide plates 22 are arranged outside the air detectors 15. The guide plates 22 have a width greater than a gap distance between two adjacent metal guide rings 11.

By arranging the guide plates 22, the guide plates 22 are subjected to transverse force when press-bending the multi-segment folding stands 21, and is stuck by the metal guide rings 11. The multi-segment folding stands 21 are prevented from getting stuck.

The device for detecting carbon emission of a passive house further includes two snap belts 23 and a snap base 24, and the snap base 24 is arranged on the metal guide ring 11 with a smallest caliber. One ends of the snap belts 23 are detachably snapped on the snap base 24, and the other ends are connected to the metal cap head 18.

The split assemblies 7 further include a plurality of secondary leads 20. The plurality of secondary leads 20 correspond one-to-one to the plurality of metal guide rings 11. One ends of the secondary leads 20 are electrically connected to the metal guide rings 11, and the other ends are connected to the metal cap head 18 by means of the main lead 19 in series.

The plurality of secondary leads 20 are arranged to be connected to the metal guide rings 11, such that during a continuous falling process of the unmanned aerial vehicle 5, the metal guide rings 11 of different sizes successively fall on the metal rain cap 2. When a nearest metal guide ring 11 does not fall on the metal rain cap 2, that is, an electrical loop of the metal guide ring 11 is not connected, and is thus in a disconnected state, an edge position of the metal rain cap 2 is determined by power-off and power-on. Position adjustment of the air detectors 16 is facilitated. A detection effect is guaranteed.

The device for detecting carbon emission of a passive house further includes a plurality of abutting plates 14 and telescopic rods 4, and the plurality of telescopic rods 4 correspond one-to-one to the plurality of air detectors 15. The telescopic rods 4 are arranged on the unmanned aerial vehicle 5 vertically, moving ends of the telescopic rods 4 penetrate the unmanned aerial vehicle 5 and extend to the bottom of the unmanned aerial vehicle 5. The abutting plates 14 are arranged on the moving ends of the telescopic rods 4. The abutting plates 14 correspond to the air detectors 15.

A working principle is as follows: when encountering a chimney 1 having a metal rain cap 2, an unmanned aerial vehicle 5 is controlled to hover in the air and then a fixed gripping assembly 16 is snap-fitted to a main lead 19. The unmanned aerial vehicle 5 is controlled to move directly above the metal rain cap 2, a metal cap head 18 is controlled to be on a cap tip of the metal rain cap 2. In this case, the unmanned aerial vehicle 5 slowly falls down, and metal guide rings 11 located at a lower position successively make contact with the metal rain cap 2. Since the metal rain cap 2 is made of metal, a current moves from a secondary lead 20 to the metal guide ring 11, then to the metal rain cap 2, and then is connected to a metal cap head 18, and a power-on loop is completed by means of the main lead 19. Furthermore, it is convenient for the present disclosure to determine an actual area of the metal rain cap 2 by means of a specific loop on which metal guide ring 11, press and bend multi-segment folding stands 21 by means of telescopic rods 4 according to a feedback, so as to make a distance from the multi-segment folding stands 21 to the metal cap head 18 close to a radius of the metal rain cap 2, then control a snap base 24 to make snap belts 23 disconnected from the snap base 24, and further to disconnect the main lead 19 from the metal cap head 18. Then, an electromagnet 8 is powered off, and a transverse telescopic rod 10 is controlled to extend, so that the two split assemblies 7 are forced to separate, then the fixed gripping assembly 16 located in the two split assemblies 7 is exposed, and then under the action of gravity, the multi-segment folding stands 21 are turned over, to make air detectors 15 just correspond to an air outlet before the metal rain cap 2 and the chimney 1.

Therefore, in the device for detecting carbon emission of a passive house, the unmanned aerial vehicle 5, the guide assembly 3 and the two landing gear assemblies 6 are arranged to cooperate with each other. The present disclosure may have a function of delivering and fixing a device for detecting carbon emission to a chimney 1 by means of an unmanned aerial vehicle, and may further effectively avoid the shielding of the metal rain cap 2 on the chimney 1 and make the detector smoothly correspond to an air outlet of the chimney 1. The present disclosure is greatly convenient for personnel to use.

What is claimed is:

1. A device for detecting carbon emission of a passive house, arranged on a metal rain cap at a top of a chimney, and comprising an unmanned aerial vehicle, a guide assembly and two landing gear assemblies, wherein the two landing gear assemblies are arrange at a bottom of the unmanned aerial vehicle, the guide assembly is arranged at a bottom of the two landing gear assemblies, the guide assembly comprises two split assemblies, the two split assemblies correspond one-to-one to the two landing gear assemblies, the split assemblies are in linked connection to the landing gear assemblies, the split assemblies comprise a plurality of metal guide rings small to large, and a connection strap, the connection strap is arranged between two adjacent metal guide rings, the plurality of metal guide rings are movably sleeved with each other, the device further comprise a fixed gripping assembly, and the fixed gripping assembly is movably arranged at the bottom of the unmanned aerial vehicle.

2. The device for detecting carbon emission of a passive house according to claim 1, wherein each landing gear assembly comprises a ring seat, a snap joint, a gear seat and a transverse telescopic rod, the transverse telescopic rods are arranged at the bottom of the unmanned aerial vehicle transversely, the gear seats are arranged at moving ends of the transverse telescopic rods, the snap joints are arranged at bottoms of the gear seats, the ring seats are detachably snapped onto the snap joints, and the ring seats are connected to the split assemblies.

3. The device for detecting carbon emission of a passive house according to claim 2, wherein each landing gear assembly further comprises an electromagnet, the electromagnets are arranged on the gear seats, and the two electromagnets located on different gear seats are attracted to each other.

4. The device for detecting carbon emission of a passive house according to claim 3, wherein the fixed gripping assembly comprises a metal cap head and a main lead, one end of the main lead is arranged at the bottom of the unmanned aerial vehicle, the other end is detachably snapped to the metal cap head, and the metal cap head is in linked connection to the split assemblies.

5. The device for detecting carbon emission of a passive house according to claim 4, wherein the fixed gripping assembly further comprises four air detectors and inwardly curved multi-segment folding stands, the four multi-segment folding stands are hinged at equal angles on the metal cap head with the metal cap head as a center, and the air detectors are arranged on one ends of the multi-segment folding stands away from the metal cap head.

6. The device for detecting carbon emission of a passive house according to claim 5, wherein the fixed gripping assembly further comprises four guide plates, the guide plates are arranged outside the air detectors, and the guide plates have a width greater than a gap distance between two adjacent metal guide rings.

7. The device for detecting carbon emission of a passive house according to claim 6, further comprising two snap belts and a snap base, wherein the snap base is arranged on the metal guide ring with a smallest caliber, one ends of the snap belts are detachably snapped on the snap base, and the other ends are connected to the metal cap head.

8. The device for detecting carbon emission of a passive house according to claim 7, wherein the split assemblies further comprise a plurality of secondary leads, the plurality of secondary leads correspond one-to-one to the plurality of metal guide rings, one ends of the secondary leads are electrically connected to the metal guide rings, and the other ends are connected to the metal cap head by means of the main lead in series.

9. The device for detecting carbon emission of a passive house according to claim 8, further comprising a plurality of abutting plates and telescopic rods, wherein the plurality of telescopic rods correspond one-to-one to the plurality of air detectors, the telescopic rods are arranged on the unmanned aerial vehicle vertically, moving ends of the telescopic rods penetrate the unmanned aerial vehicle and extend to the bottom of the unmanned aerial vehicle, the abutting plates are arranged on the moving ends of the telescopic rods, and the abutting plates correspond to the air detectors.

* * * * *